United States Patent [19]

Leung

[11] Patent Number: 4,548,212

[45] Date of Patent: Oct. 22, 1985

[54] APPARATUS FOR THERMOGRAPHIC EXAMINATIONS

[76] Inventor: Frank K. Leung, 228 E. Winchester Rd., Libertyville, Ill. 60048

[21] Appl. No.: 437,697

[22] Filed: Oct. 29, 1982

[51] Int. Cl.[4] .......................... A61B 10/00; A61F 7/00
[52] U.S. Cl. .................................... 128/736; 128/400; 128/402
[58] Field of Search .............................. 128/399–402, 128/736, 380, 766

[56] References Cited

U.S. PATENT DOCUMENTS

| | | | |
|---|---|---|---|
| 3,617,888 | 1/1962 | Weiner | 128/400 |
| 3,995,621 | 12/1976 | Fletcher et al. | 128/400 |
| 4,026,299 | 5/1977 | Sauder | 128/400 |
| 4,118,946 | 10/1978 | Tubin | 128/400 |
| 4,149,529 | 4/1979 | Copeland et al. | 128/400 |
| 4,184,537 | 1/1980 | Sauder | 128/400 |
| 4,409,991 | 10/1983 | Eldridge | 128/766 |

Primary Examiner—Lee S. Cohen
Assistant Examiner—Steven Falk
Attorney, Agent, or Firm—Emrich & Dithmar

[57] ABSTRACT

A method and apparatus for conducting thermographic examinations of localized portions of the body in which a localized area of the body is cooled. A liquid crystal film is affixed directly against the body and the localized area and film are re-cooled to a uniform temperature. The localized area of the body and the film are rewarmed and visual images appearing on the liquid crystal film, as surface temperatures increase through the sensitivity range of the film, are recorded.

7 Claims, 10 Drawing Figures

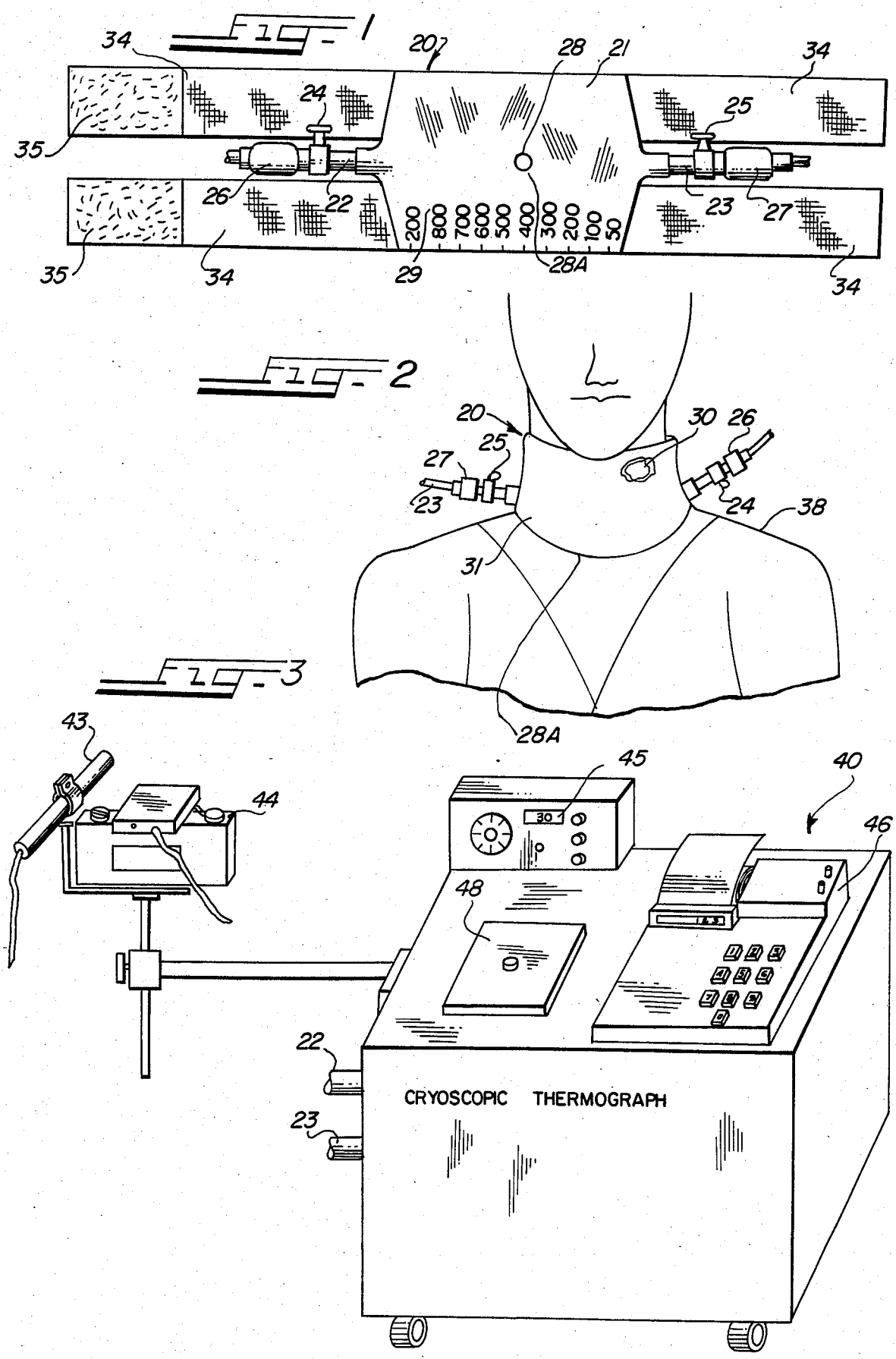

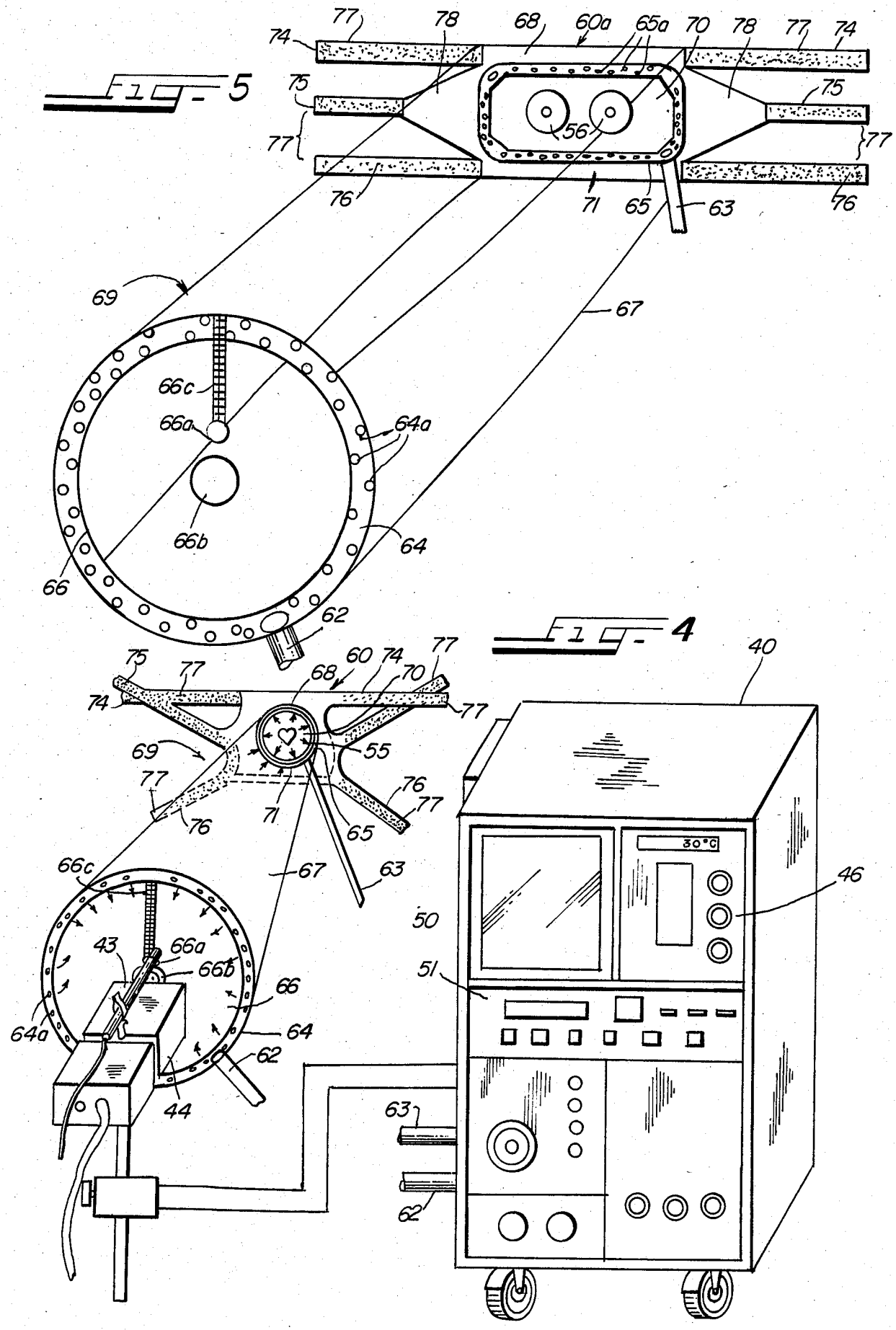

APPARATUS FOR THERMOGRAPHIC EXAMINATIONS

BACKGROUND OF THE INVENTION

The present invention relates to the art of thermographic imagery and, in particular, an apparatus and method for improving thermographic imagery through the use of controlled temperatures.

The medical community became interested in thermography as a diagnostic tool as early as 1956, when it was discovered that skin overlying breast cancer had elevated temperatures as compared to normal tissue. Several thermographic systems have become available in the United States including the AGA THERMOVISION, BOFORS M-101, SPECTROTHERM AND THERMISCOPE. Contact thermograpy utilizing liquid crystals calibrated to change color at predetermined temperatures became available in 1969. Liquid crystal films embedded in elastomeric film became available in 1980.

Despite the great advances in imaging processes, designs and electronic hardware, thermography remains plagued with numerous false negatives and false positive results which detract from its usefulness as a diagnostic tool. The problem with present thermographic techniques is related to its dependence on passive measurements of surface temperature of the subject skin. Various surface temperature variations and the presence of nonspecific isotherms occur frequently. The surface temperature of the skin is a nonspecific physiological modality, heavily influenced vascular changes, changes in biological activity, tissue conductivity, and environmental factors.

In conventional thermography, objects with the same surface temperature will appear the same because they have the same isotherms. Objects with the same surface temperature as their surroundings cannot be distinguised or separated. In conventional thermography, a tumour is usually suspected on the basis of abnormal heat patterns due to increased vascularization or asymetry. However, conventional thermography is unable to reveal any pathological signs in a large number of patients with carcinomas due to the fact that as many as 30% of carcinomas may not produce any heat and are of the same temperature as the surrounding tissue.

Although it has been recognized previously that cooling, by evaporating alcohol from skin surfaces, and air conditioned rooms, may enhance thermographic images, such techniques do not provide precise regulation of temperature of the skin surface and underlying tissue to provide fine details. Although it has been recognized that cooling accentuates temperature differentials, the optimium cooling conditions have not been known. The use of cooling wraps were suspected of practical use, as evidenced by a paper entitled: "Temperature Measurements of Localized Pathological Processes" by R. N. Larson and J. P. Gaston, but have not been investigated substantially.

SUMMARY OF THE INVENTION

The present invention provides methods and apparatus for obtaining improved thermographic images through the use of controlled temperatures.

Briefly, an embodiment of the present invention provides a method for conducting a thermographic examination of localized portions of the body including cooling the surface and underlying tissue of a localized area to 15° C. for five minutes. Affixing a liquid crystal film directly against the body. Cooling the liquid crystal sheath along with the localized area of the body for an additional 1-3, minutes again to a temperature of 15° C. to insure that the film and the surface temperature are substantially uniform. Visual images on the liquid crystal film appear as a function of elapsed time as the body surface rewarms. The thermal images can be evaluated for irregularities which would indicate underlying pathological states. The time at which the visual images appear is an indication of pathological states. For example, in thyroid examinations visual images appearing before the normal three to four minutes is an indication of hyperthyroidism, visual images appearing after three or four minutes is an indication of hypothyroidism.

The present method and apparatus need utilize a liquid crystal film of a single temperature range. Liquid crystal film usually is manufactured having a specific narrow range of temperature to which it is sensitive. In conventional thermography, the liquid crystal film must be selected on a trial and error basis until the film with the appropriate sensitivity is found. The present invention provides a method where the body surface and underlying tissues are cooled below the sensitivity of a liquid crystal film and then rewarmed such that the body surface temperatures pass through the narrow temperature range of the film providing details which conventional thermography has not been able to obtain.

An embodiment of the invention further includes an apparatus for thermally controlling body surface temperatures. Briefly, the apparatus includes a pump in communication with a source of fluid of predetermined temperature. A reservoir adapted to be positioned in close proximity and in thermal contact with the body surface includes an input line and an output line. The input line is in communication with the reservoir, fluid source and the pump for receiving fluid and directing fluid into the reservoir. The fluid received by the reservoir is circulated establishing a substantially uniform temperature throughout the reservoir and underlying body surfaces. The output line is in communication with the reservoir for receiving fluid from the reservoir and returning it to the fluid source. The reservoir includes a layer of insulating material affixed to the side distal to the body surface to aid the reservoir in maintaining a uniform temperature. Straps are affixed to the reservoir for encircling portions of the body. The straps are provided with attachment means, such as loop and hook surfaces marketed under the trademark VELCRO, for securing the reservoir securely about the body surface.

A further embodiment of the present invention utilizes air or other gases of predetermined temperature for controlling the surface temperature for localized portions of the body. Briefly, the apparatus includes a blower in communication with a source of air of predetermined temperature. An air tent, adapted to be positioned in close proximity and in thermal communication with the body surface, is in communication with the blower and air source by means of input and output lines. The air tent includes a flexible covering having a back panel, intermediate section, and a front panel. The back panel includes an opening adapted to substantially conform to the shape of the localized portion of the body. The back panel also includes a seal disposed around the edge surfaces to seal the covering in a substantially airtight manner against the body surface defining a chamber between the body surface and the covering. The input line is in communication with the source of air of predetermined temperature and the blower for receiving air and directing the air into the chamber. Air circulating in the chamber is of substantially uniform temperature to thermally control the temperature of the body surface. The output line, in communication with the chamber, receives air from the chamber and redirects the air to the air source.

The air tent further comprises a temperature sensor, such as an infrared sensing probe in communication with the chamber to monitor the temperature of the air within the chamber, skin surface or target organs. A camera for recording thermographic images is placed in communication with an opening in the covering to receive and record thermographic images appearing on liquid crystal film or solution overlying the skin surface. A digital data logger may be utilized for recording temperatures. A video recorder used in conjunction with a television camera records visual images obtained in the thermogram.

The present invention has particular application for performing thermographic examinations of the thyroid. Thus, an embodiment of the present invention further includes a liquid crystal sheath for use in thyroid thermography which is particularly applicable for use in conjunction with the cooling wraps disclosed herein. Briefly the liquid crystal sheath includes a sheet of liquid crystal film proportioned to substantially cover the front area of the neck. The liquid crystal film is substantially eliptical in shape to distribute stress equally about the film to provide a wrinkle-free surface. Four straps are affixed to the edge portions of the sheet for encircling the neck. The straps are arranged in pairs along the short lateral edge surfaces of the liquid crystal film. Each strap includes an elastic band extending from the far edges of the sheet and including hook and loop attachment surfaces, such as VELCRO, for attachment onto each other. The elastic bands secure the film firmly and resiliently to the neck while avoid stresses which would distort the film and alter thermographic images.

The controlled regulation of temperature during the performance of thermographic examinations produces dynamic images. Differing tissues rewarm or cool at different rates producing images of both thermally warm and cold structures as the surface temperature of the skin and underlying tissue changes. The temperature of the surface of the skin can be adjusted to maximize the thermal images for clarity to the extend that the images frequently correspond to an anatomical and morphological structures. Structures can be selectively imaged by altering the surface temperature. Structures with the same surface temperature but differing cellular structures can be imaged separately due to differing cooling or rewarming rates. Such differing temperature cooling or rewarming rates are useful for differentiating functional state such as hyper and hypothyroidism. Due to the regulation of surface temperature, surface temperature variations and irrelevant information can be substantially eliminated. The use of a single type of liquid crystal film within a narrow temperature range can be readily selected without consideration of other environmental factors. Further, the present invention provides means to substantially reproduce thermographic examinations under controlled conditions allowing the monitoring of treatments or pathological progression.

Other features and advantages of the present invention will be apparent from the following description and claims and are illustrated in the accompanying drawing, which by way of illustration show a preferred embodiment of the present invention and the principles thereof in what is now considered to be the best mode in which to apply these principles. Other embodiments of the invention employing the same or equivalent principles may be used and structural changes may be made as these are to those skilled in the art without departing from the present invention and purview of the appended claims.

BRIEF DESCRIPTION OF THE DRAWINGS

FIG. 1 is a front perspective view of a cooling blanket embodying principles of the present invention;

FIG. 2 is a front perspective view of the cooling blanket depicted in FIG. 1 as worn by a person about the neck;

FIG. 3 is a front perspective view of an apparatus utilized in conjunction with the cooling blanket of FIGS. 1 and 2 to perform thermographic examinations;

FIG. 4 is a front perspective view of a cooling air tent embodiment of the present invention and apparatus for thermographic examination;

FIG. 5 is a front perspective view of a cooling air blanket embodiment of the present invention;

DETAILED DESCRIPTION

The present invention will be described in detail as methods and apparatus for performing thermographic examinations upon the thyroid area of the neck and upon the breast and abdomen, due to the current interests and applicability of thermography to those areas. It is understood that the present disclosure is to be considered an exemplification of the principles of the invention and is not intended to limit the embodiment illustrated. In particular, the present invention has applications to other areas of the body as well.

It has been recognized that cooling the surface of a body by various means, such as alcohol, cold environmental temperatures, or circulating air upon the body surface, may enhance thermal images. However, the narrow range of surface temperature which would produce the maximum temperature contrast between an object and its surroundings remained unknown. The cooling means of the prior art were also purely tolerated by subjects, particularly those sensitive to low temperature such as those afflicted with hypothyroidism. The present invention provides a precise regulation of local skin surface temperature and the underlying deep seated structures in order that optimal thermal images are obtained. For a localized area of the human body, each structure generally has a different thermal conductivity, a different surface temperature, a different depth and other differences which influence thermal examination. In order to separate thermal images of differing internal structures the present invention allows the temperature of the skin surface and underlying tissues of a localized area of the body to be selectively raised or lowered. Images of different tissues thereby appear in a predictable sequence.

Figure 6:
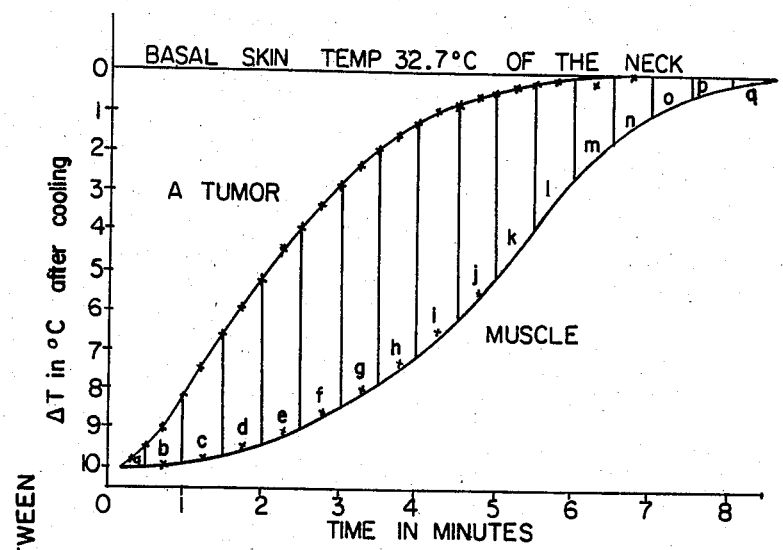
FIG. 6 is a graph depicting the change in temperature of tumors and muscles of the neck.
Figure 7:
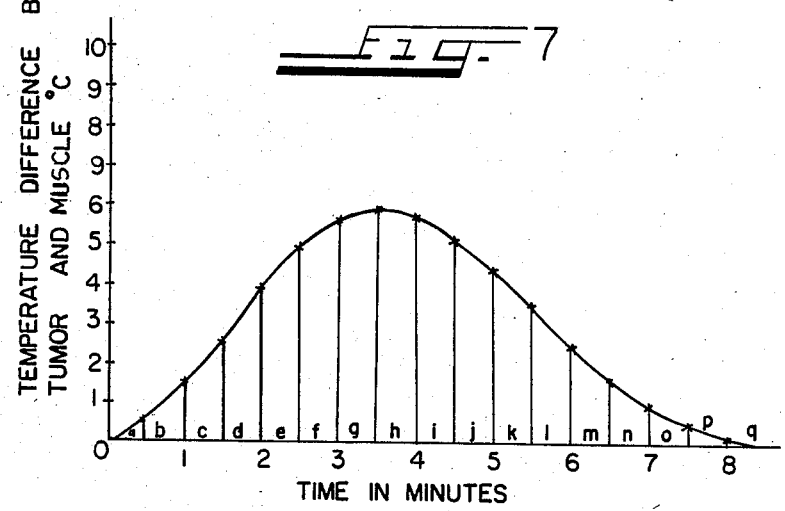
FIG. 7 is a graph depicting the difference in temperatures over time between tumors and muscles of the neck.

The thyroid gland is an ideal organ for thermographic studies because it is superficially located and richly vascularized. Referring now to FIG. 6, if the surface of the neck is cooled the skin temperature over a tumor will warm at a faster rate than normal tissue and muscle. Referring now to FIG. 7 the maximum difference in surface skin temperature overlying muscle and tumors will appear predictably within three or four minutes, allowing one to obtain thermal images of maximum clarity which differentiate the tumor from surrounding tissue during that period of time.

Figure 8:
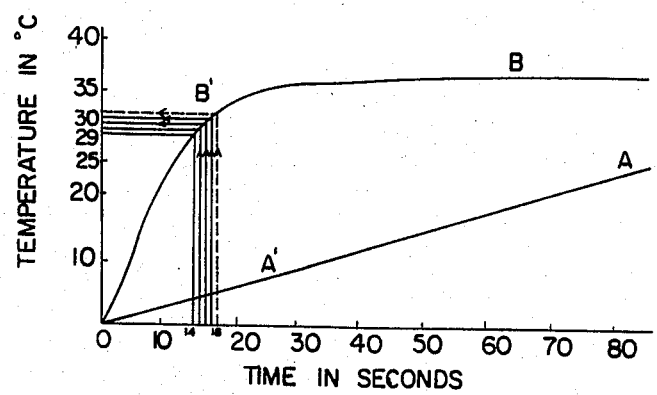
FIG. 8 illustrates temperature changes in tumors and cysts.

Further, controlled local cooling of the skin surface allows for the differentiation between tumors and cysts. Referring now to FIG. 8, where line B refers to the surface temperature over a tumor and line A refers to the surface temperature of a cyst, if the tumor and cyst are cooled uniformly to a temperature of 0° C. then allowed to rewarm themselves by the core body temperature, the tumor will rewarm itself much quicker than the cyst.

Liquid crystal elastomer sheeting typically has a temperature capability between 28°–32° C. At 28° C. the color of the infrared thermography is dark brown, at 29° C. red, at 30° C. yellow, at 31° C. green, and at 32° C. blue. Returning to FIG. 8, at 14 seconds after rewarming the color of the infrared thermography will start to change. At 18 seconds the overlying skin above the tumor will warm to 32° C. appearing blue on the liquid crystal film whereas the skin overlying the cyst with a temperature of 5° C., is below the sensing ability of the liquid crystal film, remains black in color. It will take more than 80 seconds after rewarming before the skin surface over the cyst begins to change color and appear on the liquid crystal film. Thus, it is feasible to differentiate between a tumor and a cyst independent of their original surface temperature.

Further, the elapse rewarming time before thermal images appear as an indication of pathological states. In a normal subject thyroid images having maximum clarity appear between three to four minutes. In hypothyroid subjects the elapsed time will be extended shortened.

Figure 9:
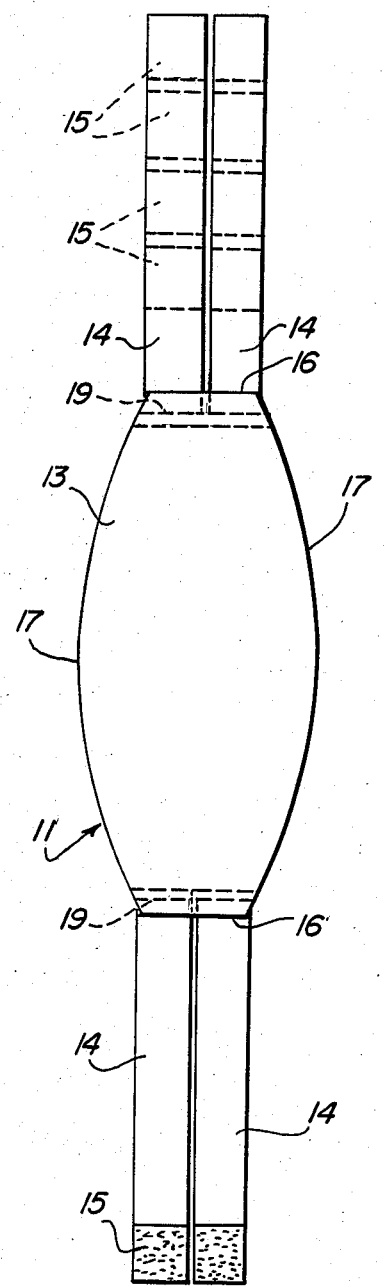
FIG. 9 is a perspective view of the liquid crystal sheath in accordance with the present invention.
Figure 10:
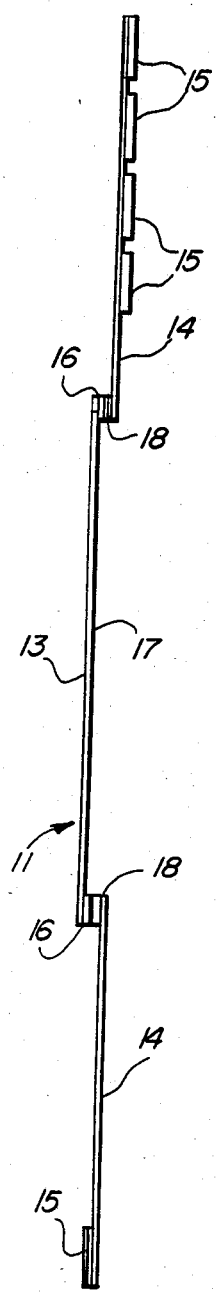
FIG. 10 is a cross-sectional view of the liquid crystal sheath of the present invention.

Turning now to an apparatus for performing thermographic examinations of the thyroid, an embodiment of the present invention includes a liquid crystal sheath for use in thyroid thermography which is particularly applicable for use in conjunction with the cooling apparatus to be discussed later in the application. Referring now to FIGS. 9 and 10 the liquid crystal sheath, generally designated 11, includes a sheet of liquid crystal film 13 proportioned to substantially cover the front area of the neck. The liquid crystal film 13 is substantially eliptical in shape to distribute forces equally producing a substantially wrinkle-free surface. For adults, the eliptical film 12 has a small diameter of approximately four centimeters in length and a long diameter of approximately eight and one half centimeters. The liquid crystal film 13 has short lateral edge surfaces 16, which can be squared off as shown, and long rounded top and bottom edge surfaces 17. Four straps are affixed to the edge portions of the liquid crystal film 13, arranged in pairs along the short lateral edge surfaces 16, for encircling the neck. Each elastic band 14 includes hook and loop attachment surfaces 15, such as those commonly marketed under the trademark "VELCRO", for affixing the elastic bands 14 onto each other in an infinitely adjustable manner. The elastic bands 14 are affixed to the film 13 by means of foam 18 and metallic fasteners such as staples 19. The elastic bands provide a firm yet resilient pressure on the edge surfaces of the liquid crystal film 13 to hold the liquid film 13 firmly and tightly against the skin surface of the neck.

An embodiment of the present invention further includes an apparatus for thermally controlling localized body temperatures. Referring now to FIGS. 1, 2 and 3, a cooling blanket for use in controlling the body temperature of the neck area for thyroid thermography is generally designated by the numeral 20. The cooling blanket 20 includes a flexible reservoir 21 having a proximal surface 29, for positioning in close proximity and in thermal contact with the body surface about the neck, and an opposite distal surface 30 away from the body. Extending laterally from opposite sides of the reservoir 21 is an input line 22 and an output line 23. Input line 22 and output line 23 are in communication with the interior of the reservoir 21. Input line 22 receives fluid of a predetermined temperature and directs the fluid into the reservoir 21 where it is circulated to obtain a substantially uniform temperature throughout before exiting through the output line 23. The input line 22 is provided with an input valve 24 to control the fluid flow and pressure through the reservoir. A small resilient input reservoir 26 is positioned in the input line 22 to absorb the pressure as the input valve 24 is adjusted and to reduce turbulence. Similarly, an output valve 25 is positioned in communication with the output line 23 to control the fluid pressure within the reservoir 21. A small resilient reservoir 27 is placed within the output line 24 to absorb changes in pressure and reduce turbulence. The input and output valves 24 and 25 allow the pressure in the reservoir to be maintained at a level where the reservoir 21 compliant to conform to the surface features of the neck. Over-inflation of the reservoir 21 forces the reservoir 21 to ballon outward from the neck surface such that uniform temperatures are not obtained. If flow is insufficient, the reservoir 21 will not provide substantially equal distribution of fluid and will also result in nonuniform temperatures.

A temperature sensing device, such as a thermister 28 is positioned about the proximal surface of the reservoir 21 to allow the monitoring of the body surface temperature while the cooling blanket is being worn 20. Referring now specifically to FIG. 2 where the cooling blanket 20 is depicted as worn by a subject 38 the electrical wire 28A leading to the thermister 28 can be seen protruding from the cooling blanket where it can be connected to the thermograph control equipment 40 depicted in FIG. 3. The input and output lines 22 and 23 respectively protrude outwardly from the cooling blanket 20 allowing the input and output valves 24 and 25 respectively to be easily manipulated by an operator of the equipment.

An insulating layer 31 is positioned upon the distal surface of the reservoir 21 to facilitate the maintenance of uniform temperatures throughout the reservoir 21. The insulating layer 31 can be extended in the forms of straps 34 fashioned to substantially encircle the next area. The straps 34 are equipped with hook and loop attachment surfaces, marketed under the trademark VELCRO, for attaching the straps 34 onto each other at an infinite number of positions to allow the device to be worn by subjects with differing size neck areas.

Referring now to FIG. 3 an embodiment of the present invention includes thermograph control equipment 40. The thermograph control equipment 40 includes a source of fluid 48, preferably water and glycerol proportioned in equal amounts, in communication with a pump (not shown) which pumps the fluid through input line 22 to the cooling blanket 20. Fluid flowing from the reservoir 21 into the output line 23 is returned by the output line 23 to the fluid source 48. The thermograph control equipment 40 further includes an infrared sensor 43 for detecting the temperature of the neck surface and underlying tissue and a camera or other visual recorder 44 for recording visual images that appear upon the liquid crystal film. The thermograph control equipment 40 includes a data recorder 46 and timer 45 for recording elapsed time of photographs and the temperature readings of the infrared sensing device.

In utilizing the apparatus, the cooling blanket 20 is wrapped about the neck area and secured in place by attaching straps 34. Cooling fluid is circulated through the reservoir 21 by means of input and output lines 22 and 23. After a predetermined temperature of the skin surface is obtained, preferably 15° C., as indicated by the temperature sensing device 28, the cooling blanket 20 is removed and the liquid crystal sheath as previously described is affixed about the neck area. The cooling blanket 20 is once again applied to the neck area to bring the liquid crystal sheath and the local skin area again to a uniform temperature of approximately 15° C. After the liquid crystal sheath and the neck area are recooled for approximately 1-3 minutes, the cooling blanket 20 is removed and visual images on the liquid crystal sheath are recorded by the camera 44 as the skin surface and underlying tissues rewarm. The elapsed rewarming time, visual images and temperature readings are recorded by the data recorder 46 at regular intervals as determined by the timer 45.

Further embodiments of the present invention utilize air or other gases of predetermined temperature for controlling the surface temperature of localized portions of the body. Referring now to FIG. 4 an air tent apparatus generally designated by the numeral 60, is adapted to be positioned in close proximity to the body surface to circulate air of predetermined controlled temperature. The air tent 60 includes a flexible cover 69 having the following major elements: a back panel 68, a front panel 66, and an intermediate section 67 (not necessarily drawn to scale). The back panel 68 includes an opening 70 for exposing a localized area of the body surface when the back panel is placed in close proximity thereto. The back panel 68, front panel 66, and intermediate section 67 define a chamber 71 through which air of controlled predetermined temperature is circulated. An input line 62 is in communication with the chamber 71 by means of a porous tube 64 which encircles the front panel 66. The input porous tume 64 includes a plurality of holes 64a to distribute air from the input line 62 substantially equally about the front panel 66 with minimal turbulence. Air entering chamber 71 circulates towards the back panel 68 where it is received by an output porous tube 65 encircling the opening 71. The output porous tube 65 includes a plurality of openings (not shown) to receive the circulating air. Output line 63 in communication with the output porous tube 65 receives the air and shunts the air to the thermograph control equipment 40 equipped with a source of controlled temperature air (not shown).

Back panel 68 is preferably formed of a resilient foam material which allows the back panel to sealably engage the body surface. Affixed to the back panel 68 are straps 74 through 76 to encircle the neck area and secure the back panel in sealing engagement with the body surface. Thus, straps 74, jutting horizontally from the upper portion of the back panel 68, encircle the upper neck area. Middle straps 75, jutting laterally upward from the mid section of back panel 68, extend over the shoulder. Lower straps 76, jutting laterally downward from the back panel 68, wrap under the arm. Each strap 74–76 include hoop and loop attachment surfaces 77, such as those marketed under the trademark VELCRO, to affix the straps 74–76 onto each other to securely position the back panel 68 about the neck surface.

Front panel 66 is provided with openings 66A and B adapted to receive an infrared temperature sensing device 43 and a television or photographic camera 44. A zipper 66C facilitates the positioning of the camera and infrared sensing device 43 in communication with the interior chamber 71. It will be recognized by those skilled in the art, that the camera and infrared sensing device need not be positioned in the front panel, but may be positioned anywhere in communication with the chamber 71 to observe thermographic changes in the liquid crystal film positioned upon the subject. It will also be recognized that although the covering 69 is referred to as being flexible and resilient, providing flexible lightweight equipment, rigid covers would operate in substantially the same manner and are considered within the purview of the present invention. It is also feasible to affix liquid crystal film across opening 70 in back panel 68 to close chamber 71 incorporating the film into the cover 69.

The air tent apparatus 60 allows the surface temperature of the skin and an overlying liquid crystal film to be controlled while simultaneously recording thermal images by means of camera 44. Thus, cryoscopic thermograph 40 includes a television screen for monitoring thermographic images and an infrared temperature sensing device 43. An infrared temperature sensing device 43 available from Magna Instruments Corporation. The infrared temperature measuring device 43 is capable of sensing the air temperature within the chamber 71 or the temperature of the skin surface and the target organ of a subject wearing the air tent 60. The temperatures of the air and the skin can be recorded on a data recorder 46 of the thermograph control equipment 40 while thermographic images are recorded upon a video recorder 51 and displayed upon a television screen 50. The use of the air tent 60 allows for a duplication of thermographic examinations with fine details in a controlled setting to allow the monitoring of treatment or pathological changes. The air tent 60 allows thermographic images to be readily taken while the subject's skin is cooled or warmed.

Referring now to FIG. 5, an air tent apparatus 60A, similar to that previously described, is illustrated for thermographic examinations of the chest and abdomen, and particularly the breasts. The modified air tent 60A similarly includes a front panel 66, an intermediate section 67 and a back panel 68 defining a chamber 71. Back panel 68 includes a more rectangular opening 70 to expose the breast and axillae to the view of a camera and an infrared temperature sensing device (not shown in FIG. 5) which can be placed in communication with chamber 71 by means of openings 66A and B in front panel 66.

Preferably back panel 68 is formed from a foamed resilient material which allows the back panel to be placed in sealing engagement against the body surface. The back panel 68 is held securely in engagement with the body surface by means of straps 74, 75 and 76. Middle strap 75 includes a triangular portion 78. The triangular portion 78 extends substantially from the upper and lower areas of the back panel 68 and narrows to form the strap 75 to distribute stress equally about the back panel 68. Straps 74, 75 and 76 include hook and loop attachment surfaces about their length for affixing the straps onto each other to encircle and secure the air tent apparatus 60A about the upper body area. Input line 62, input porous tube 64, output line 63, and output porous tube 65 act similarly to the air tent 60 described in FIG. 4, to blow air of controlled predetermined temperature into the chamber 71 by means of the input line and input porous tubes 64 circulating the air, circulating the air towards the output porous tube 64 where the air is received and shunted by output line 63 back to the source of controlled air within the thermograph control equipment 40.

Preferably in using either of the air tent apparatuses 60 or 60A air circulating within the system is dehumidified so as not to interfere with infrared temperature reading or with thermographic readings. Preferably the infrared sensing probe measures and monitors the temperature of the target organ and the temperature of the cooling blanket or skin surface. The rate of temperature change during the procedure is continuously monitored and recorded in a data logger 46 equipped with a printer. Data loggers 46 are available from companies such as Electronic Control Design, Inc. or Minilogger. The camera should have a macrolens and low light capability. Liquid crystal film is inherently shiny creating problems in lighting. Preferably a cross field polarizing light should be used.

Thus, the present invention includes methods and apparatus for performing thermographic examinations which can be readily reproduced to monitor the progression of treatment or disease and yet is inexpensive, very rapid in obtaining results, and simple in operation. Thus, while the preferred embodiment of the present invention has been illustrated and described, it is understood that it is capable of variation and modification and should not be limited to the precise details set forth, but should include such changes and alterations as fall within the purview of the following claims.

I claim:

1. An apparatus for thermally controlling local body temperature for use in conjunction with a source of air of a predetermined temperature; and a blower means in communication with said source for circulating said air of a predetermined temperature comprising:

an input line means for communicating with said air source and blower means for receiving air;

an air tent including a cover and sealing means, said cover having edge surfaces adapted to substantially conform to the shape of a localized portion of the body and having a first opening therein which exposes the portion of the body to be thermally controlled, said sealing means disposed around said edge surfaces to seal said cover in a substantially airtight manner against a body surface and defining a chamber between said body surface and said cover, said cover further having a second opening in an overlying position with said first opening, with said second opening adapted to receive the lens of a camera to photograph said exposed portion of the body, and with said chamber in communication with said input line means to receive air of a predetermined temperature;

an output line means in communication with said chamber for receiving said air from said chamber; and air tent securing means to secure said air tent in close proximity to said body surface to direct air directly onto the exposed portion of the body and to thereby control the body temperature of the exposed portion of the body.

2. The apparatus of claim 1 further comprising temperature sensing means in communication with said chamber.

3. The apparatus of claim 1 further including said camera, said camera being in communication with said second opening in said chamber for recording thermographic images on a liquid crystal film positioned on said exposed portion of the body.

4. The apparatus of claim 1 wherein said cover has a third opening adapted to receive an infrared sensing probe in communication with said chamber for measuring the temperature within said chamber.

5. The apparatus of claim 1 further including said camera, said camera is an infrared camera mounted in communication with said chamber.

6. The apparatus of claim 3 further including a data logging means for recording said body temperature and visual images of said camera.

7. The apparatus of claim 2 wherein said temperature sensing means is a thermister for determining the local body temperature of said exposed portion of the body.

* * * * *

UNITED STATES PATENT AND TRADEMARK OFFICE
CERTIFICATE OF CORRECTION

PATENT NO. : 4,548,212

DATED : October 22, 1985

INVENTOR(S) : Frank K. Leung

It is certified that error appears in the above-identified patent and that said Letters Patent is hereby corrected as shown below:

```
Column 1, line 32, after "influenced" insert --by--;
Column 1, lines 38-39, delete "distinguised" insert
                                             --distinguished--;
Column 1, line 40, delete "tumour" insert --tumor--;
Column 2, line 4, delete ",";
Column 3, line 48, delete "extend" insert --extent--;
Column 4, line 1, delete "drawing" insert --drawings--;
Column 5, line 10, delete "muscle" insert --muscles--;
Column 6, line 40, delete "ballon" insert --balloon--;
Column 7, line 57, delete "tume" insert --tube--.
```

Signed and Sealed this

Twenty-fifth Day of February 1986

[SEAL]

Attest:

DONALD J. QUIGG

Attesting Officer     Commissioner of Patents and Trademarks